(12) United States Patent
Meikle

(10) Patent No.: US 11,076,969 B2
(45) Date of Patent: Aug. 3, 2021

(54) SIMULATED BREAST FEEDING SYSTEM

(71) Applicant: Little Latchers, LLC, Brooklyn, NY (US)

(72) Inventor: Kimberly Meikle, Brooklyn, NY (US)

(73) Assignee: Little Latchers, LLC, Brooklyn, NY (US)

( * ) Notice: Subject to any disclaimer, the term of this patent is extended or adjusted under 35 U.S.C. 154(b) by 586 days.

(21) Appl. No.: 15/933,302

(22) Filed: Mar. 22, 2018

(65) Prior Publication Data

US 2019/0060088 A1 Feb. 28, 2019

Related U.S. Application Data

(60) Provisional application No. 62/543,150, filed on Aug. 23, 2017.

(51) Int. Cl.

| | |
|---|---|
| *A61F 2/52* | (2006.01) |
| *A61J 7/00* | (2006.01) |
| *A61J 11/00* | (2006.01) |
| *A61B 5/0205* | (2006.01) |
| *A61B 5/16* | (2006.01) |
| *A61B 5/00* | (2006.01) |
| *A61J 1/14* | (2006.01) |
| *A61J 13/00* | (2006.01) |
| *A61J 9/06* | (2006.01) |
| *A61F 2/68* | (2006.01) |
| *A41D 1/215* | (2018.01) |

(Continued)

(52) U.S. Cl.
CPC .......... *A61F 2/52* (2013.01); *A61B 5/02055* (2013.01); *A61B 5/165* (2013.01); *A61B 5/7267* (2013.01); *A61J 1/1462* (2013.01); *A61J 7/0015* (2013.01); *A61J 9/0676* (2015.05); *A61J 11/0005* (2013.01); *A61J 13/00* (2013.01); *A41D 1/215* (2018.01); *A61B 5/02438* (2013.01); *A61B 5/0816* (2013.01); *A61B 5/1112* (2013.01); *A61B 5/7264* (2013.01); *A61B 2503/045* (2013.01); *A61B 2560/0406* (2013.01); *A61B 2562/0219* (2013.01); *A61B 2562/0223* (2013.01); *A61B 2562/0271* (2013.01); *A61F 2002/526* (2013.01); *A61F 2002/689* (2013.01); *A61F 2002/705* (2013.01); *A61J 9/00* (2013.01)

(58) Field of Classification Search
CPC .......... A41C 3/04; A61J 9/0676; A61J 9/0669
USPC .......................................................... 450/37
See application file for complete search history.

(56) References Cited

U.S. PATENT DOCUMENTS

| | | | | |
|---|---|---|---|---|
| 4,776,546 | A | * 10/1988 | Goldson | A61J 9/00 224/148.4 |
| 4,965,888 | A | * 10/1990 | Jones | A61J 9/00 2/104 |

(Continued)

*Primary Examiner* — Gloria M Hale
(74) *Attorney, Agent, or Firm* — Patent Ventures, LLC

(57) ABSTRACT

The breastfeeding device present in the invention, simulates natural breastfeeding experience and delivers fluid, milk or infant formula to the nursing infant in a contactless or latch free manner than any prior art in this field. This device integrates physical sensors to the breastfeeding device and includes a neck strap, refillable housing chamber that contains fluid, a tubing that connects the housing chamber to a prosthetic nipple via a sealing attachment and a prosthetic nipple for infant latching to nurse. The invention is a notable step forward in creating an effective, safe and contactless nursing which mitigates and prevents bruised, sore nipples or engorged breasts.

20 Claims, 4 Drawing Sheets

(51) Int. Cl.
  *A61F 2/70* (2006.01)
  *A61B 5/11* (2006.01)
  *A61B 5/024* (2006.01)
  *A61B 5/08* (2006.01)
  *A61J 9/00* (2006.01)

(56) References Cited

U.S. PATENT DOCUMENTS

| | | | | |
|---|---|---|---|---|
| 5,086,517 | A * | 2/1992 | Jones | A61J 9/00 |
| | | | | 2/104 |
| 5,690,679 | A * | 11/1997 | Prentiss | A61J 9/00 |
| | | | | 215/11.6 |
| 5,993,479 | A * | 11/1999 | Prentiss | A61J 9/00 |
| | | | | 606/236 |
| 6,669,064 | B2 * | 12/2003 | Perricone | A61J 9/001 |
| | | | | 215/11.3 |
| 7,107,706 | B1 | 9/2006 | Bailey et al. | |
| 7,204,041 | B1 | 4/2007 | Bailey et al. | |
| 7,621,797 | B1 * | 11/2009 | Hershkovich | A41C 3/04 |
| | | | | 450/36 |
| 9,028,407 | B1 | 5/2015 | Bennett-Guerrero | |
| 10,463,082 | B2 * | 11/2019 | Boele | A41C 3/04 |
| 10,780,037 | B2 | 9/2020 | Myntti | |
| 2004/0010311 | A1 | 1/2004 | Reynolds et al. | |
| 2005/0261738 | A1 * | 11/2005 | Garrett | A61J 17/10 |
| | | | | 606/234 |
| 2008/0248718 | A1 * | 10/2008 | Henke | A41C 3/04 |
| | | | | 450/38 |
| 2009/0194116 | A1 * | 8/2009 | Pacini | A61J 13/00 |
| | | | | 128/890 |
| 2009/0261054 | A1 * | 10/2009 | Shelby | A61J 11/04 |
| | | | | 215/11.3 |

* cited by examiner

SIMULATED BREAST FEEDING SYSTEM

CROSS-REFERENCE TO RELATED APPLICATION

This application claims priority to U.S. Provisional Patent Application Ser. No. 62/653,150 filed on Aug. 23, 2017 which is incorporated herein in its entirety.

FIELD OF THE INVENTION

The present invention relates to a simulated breastfeeding device for effective nursing of infants. More particularly, the invention relates to a device and method for enabling a parent to nurse an infant in a safe and efficient manner.

BACKGROUND OF THE INVENTION

There is a tremendous psychological and emotional benefit that comes along with breastfeeding that aids in infants' development that they do not get from bottle feeding alone, in addition to the psychological and emotional benefit to the parent of bonding with the child. However, there are many instances in which parents are unable to breastfeed their babies. For instance, women who have had mastectomies may be unable to breastfeed, and some diseases or medications require women to forego breastfeeding for the safety of their child. Adoptive parents of newborn babies also do not have the ability to breastfeed. Thus, many parents miss out on the bonding experience of breastfeeding their infant, and their infants do not receive the benefits of bonding with their mother.

In many cases, the time taken to establish milk supply ranges between four to six weeks after a baby's birth. This also requires the mother to breastfeed the infant continuously, around the clock. Such continued breastfeeding where the infant remains in constant contact with the mother's breast and nipples could, in many instances, result in rashes, irritability caused by the swelling of the nerves, and bleeding around the nipples or nerves due to incorrect latching by the infant. The World Health Organization estimated that approximately 60% of mothers who stopped breastfeeding did so earlier than desired and the early termination was positively associated with mother's concerns regarding difficulties with lactation, swollen breasts, irritability, rashes, etc. There are no products in the market that facilitate latch free or contactless nursing: simulated breast-feeding obviating the need of mouth-nipple contact, thereby avoiding or mitigating rashes, irritability, or swelling in the nipple region of the mother. This void, in turn, results in mothers giving up on the chance to breastfeed and resort to only formula feeding or exclusive pumping.

Other devices have been proposed to solve this problem, such as wearable baby bottles that can strap to the chest. These solutions can be clunky and unnatural and take away the skin-to-skin connection of natural breastfeeding. The simulated breast-feeding product from Medela include, a compact disposable device which provides a suckling infant with a liquid diet supplement simultaneously with normal breastfeeding. However, it still requires direct contact with the mother's breasts and hence does not address the irritability and swollen nerves issue that prolonged breastfeeding tends to cause in mothers.

SUMMARY OF THE INVENTION

In an embodiment of the invention, the breastfeeding device simulates natural breastfeeding experience and delivers fluid, milk or infant formula to the nursing infant in a contactless or latch free manner than any prior art in this field. This device integrates physical sensors to the breastfeeding device and includes a neck strap, refillable housing chamber that contains fluid, a tubing that connects the housing chamber to a prosthetic nipple via a sealing attachment and a prosthetic nipple for infant latching to nurse. The invention is a notable step forward in creating an effective, safe and contactless nursing which mitigates and prevents bruised, sore nipples or engorged breasts.

More specifically, the present invention relates to a system to breastfeed an infant to nurse in a safe and effective manner. In an embodiment, the device includes a neck strap, an attachable refillable housing chamber with a sealing contraption at one end, a tube linking the refillable housing chamber to a prosthetic nipple. Further yet, in an embodiment of the invention, the prosthetic nipple of the system comprises of an opening to deliver the fluid from the refillable housing chamber to an infant to promote a non-latching simulating breastfeeding experience. Additionally, in an embodiment of the invention, the device may include a sensor, a network interface, a processor, an analyzing module, a non-transitory storage element with encoded instructions coupled to the processor configure the system to receive an input parameter from an infant or user, determine a physical, physiological or emotional state of the infant/user via the analyzing module and dynamically interact with the infant/user based on a determined output.

The sensor activity of the system corresponds to at least one of aspects and advantages of this invention and may be realized in other applications, aside from the intended application of nursing/feeding an infant. Examples of other pertinent applications that may exploit the aspects and advantages of this invention include, but are not limited to, monitor the life and volume of fluid consumed by the infant during the feeding time, to monitor if the infant falls asleep while nursing, or if the infant is feeding for comfort or hunger. The device could also be used to sense infant temperature to trigger an alarm when it detects an abnormality in respiration rhythms or abnormal body temperatures.

The invention will typically employ one or more sensors, one or more processors (e.g. compute processors such as microprocessors, and the like), a network interface, an analyzing module to analyze and monitor the characteristics of infant nursing and feeding. These characteristics include feeding, latching, sleeping and the like. The invention may use data from these various sensors and processors to establish a baseline of what is "normal" for these types of activities. These baselines may be established across various characteristics and/or customized for each infant to establish an infant profile. These baselines may also be adjusted for different situations that may be possible outcomes.

DETAILED DESCRIPTION OF DRAWINGS

The present invention will now be described more fully with reference to the accompanying drawings, in which embodiments of the invention are shown. However, this disclosure should not be construed as limited to the embodiments set forth herein. Rather, these embodiments are provided so that this disclosure will be thorough and complete, and will fully convey the scope of the disclosure to those skilled in the art. Like numbers refer to like elements throughout.

In the following description, for purposes of explanation, numerous specific details are set forth in order to provide a thorough understanding of the invention. It will be apparent, however, to one skilled in the art that the invention can be practiced without these specific details.

Reference in this specification to "one embodiment" or "an embodiment" means that a feature, structure, or characteristic described in connection with the embodiment is included in at least one embodiment of the invention. The appearances of the phrase "in one embodiment" in various places in the specification are not necessarily all referring to the same embodiment, nor are separate or alternative embodiments mutually exclusive of other embodiments. Moreover, various features are described which may be exhibited by some embodiments and not by others. Similarly, various requirements are described which may be requirements for some embodiments but no other embodiments.

Overview

The primary purpose of the disclosure is to simulate a contactless latch-free breastfeeding experience without causing rashes, irritability, pain or swelling to the mother's breast to ensure a safe nursing experience. This experience helps the parent transition effortlessly into the role of a new parent and simultaneously enjoy the bonding time.

Exemplary Environment

Figure 1:
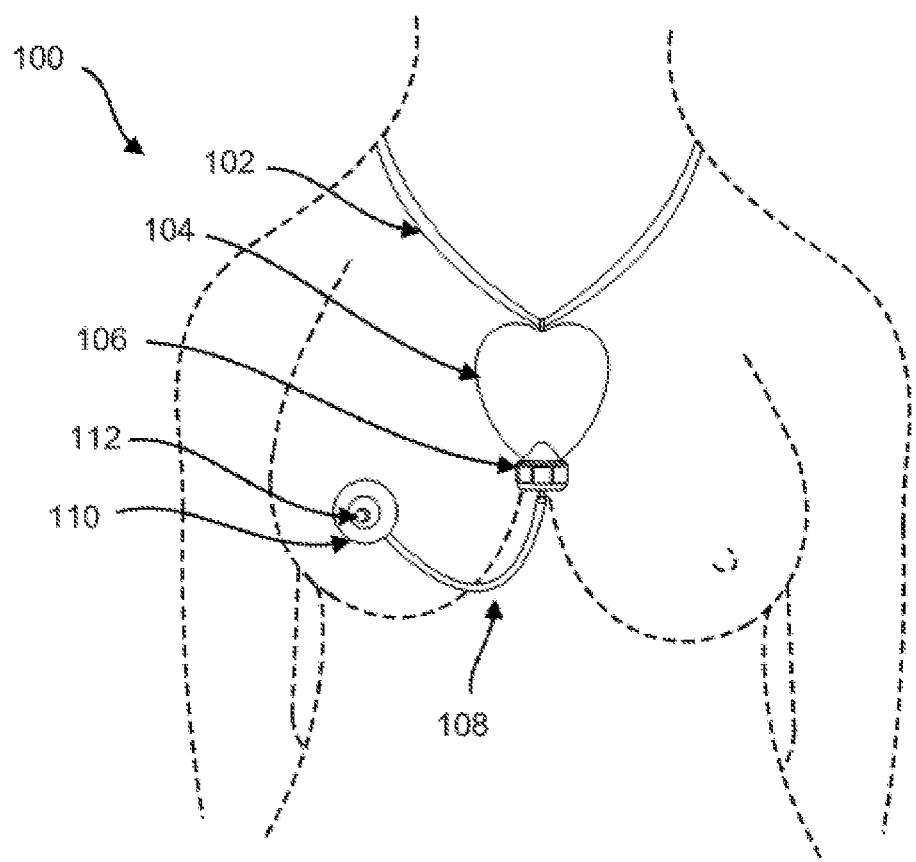
FIG. 1 describes an exemplary embodiment of the invention.

FIG. 1 illustrates an exemplary environment in which various embodiments of the present invention can be practiced. In an embodiment of the invention, a simulating breast-feeding system 100 comprises of a neck strap 102, an attachable refillable housing chamber 104 with a sealing contraption 106 at one end, a tube 108 linking the refillable housing chamber 104 to a prosthetic nipple 110 wherein, the prosthetic nipple 110 comprises of an opening 112 to deliver the fluid from the refillable housing chamber 104 to an infant to promote a non-latching simulating breastfeeding experience to prevent bruised, sore nipples or engorged breasts. Additionally, this system solves the problem of the lack of ability for communities such as, but not limited to, breast cancer survivors, LGBTQ, adoptive parents as well as family members to engage in the bonding breastfeeding experience with the infant.

Further yet, in an additional embodiment of the invention, the breast-feeding system may comprise of a sensor, a network interface, a processor, an analyzing module, a non-transitory storage element coupled to the processor and encoded instructions stored in the non-transitory storage element, wherein the encoded instructions when implemented by the processor, configure the system to receive an input parameter from an infant/user to determine a physical, physiological or emotional state of the infant/user by mapping the received input parameter with a pre-stored set of parameters via the analyzing module and dynamically interacting with the infant/user based on a determined output.

Additionally, in an embodiment of the invention, the system may further comprise of a sensor attached to at least one of, but not limited to, a sealing contraption, neck strap, prosthetic nipple, tubing or the refillable housing. To enable continuous monitoring, the user uses a sensor attached on any one of, but not limited to, the sealing contraption 106, neck strap 102, prosthetic nipple 110, tubing 108 or the refillable housing chamber 104 and a mobile communication device (not shown). The sealing contraption 106, neck strap 102, prosthetic nipple 110, tubing 108 or the refillable housing chamber 104 are typically embedded/equipped with one or more motion sensors, physiological sensors and environmental sensors. Examples of these sensors include, but are not limited to accelerometers, gyroscopes, inclinometers, geomagnetic sensors, global positioning systems, impact sensors, microphones, cameras, heart rate monitors, pulse oximeters, blood alcohol monitors, respiratory rate sensors, transdermal sensors, galvanic skin response (GSR) sensors and electromyography (EMG) sensors. In an embodiment of the present invention, the data captured by the one or more sensors is sent to the processing unit through the network. Further yet, the simulating breast-feeding system may comprise of a sensor to monitor fluid consumption to gauge if, the infant is feeding for comfort or hunger. Additionally, in another embodiment of the invention, the simulating breast-feeding system may comprise sensors to detect at least one of, but not limited to, infant temperature, heart rate, pulse rate, respiratory patterns or rhythms or accuracy of latching.

Further yet, the simulating system 100 may be worn on one or more body parts of the user, such as wrist, waist, neck, arm, leg, abdomen, chest, thigh, head, ear and fingers as well as attached to a plurality of attachments such as, but not limited to, an armband, headband, backpack worn by the user.

The mobile communication device is a portable device that has the capability of communicating over the network in real time, presenting periodic surveys to the user and receiving response from the infant/user on the periodic surveys. Examples of the mobile communication device include, but are not limited to, a smartphone, a tablet, a personal digital assistant (PDA) and a mobile phone.

In an embodiment of the present invention, the data captured by the one or more sensors of the simulating breast-feeding system 100 is first sent to the mobile communication device and thereby, sent to the processing unit over the network. The simulating breast-feeding system 100 communicates with the mobile communication device over a short range wireless communication medium. Examples of the short range wireless communication medium include Bluetooth, ZigBee, Infrared, Near Field Communication (NFC) and Radio-frequency identification (RFID).

The network may be any suitable wired network, wireless network, a combination of these or any other conventional network, without limiting the scope of the present invention. Few examples may include a LAN or wireless LAN connection, an Internet connection, a point-to-point connection, or other network connection and combinations thereof. The network may be any other type of network that is capable of transmitting or receiving data to/from host computers, personal devices, telephones, video/image capturing devices, video/image servers, or any other electronic devices. Further, the network is capable of transmitting/sending data between the mentioned devices. Additionally, the network may be a local, regional, or global communication network, for example, an enterprise telecommunication network, the Internet, a global mobile communication network, or any combination of similar networks. The network may be a combination of an enterprise network (or the Internet) and a cellular network, in which case, suitable systems and methods are employed to seamlessly communicate between the two networks. In such cases, a mobile switching gateway may be utilized to communicate with a computer network gateway to pass data between the two networks. The network may include any software, hardware, or computer applications that can provide a medium to exchange signals or data in any of the formats known in the art, related art, or developed later.

In an embodiment of the present invention, the processing unit receives the sensor data from the simulating breast-feeding system 100 and response on the periodic surveys from the user/infant. Thereby, the processing unit correlates the sensor data with the response on periodic surveys, generates reports corresponding to the physical, physiological or emotional state of the user/infant and sends the reports and other relevant data to the user. These reports enable the user to track/monitor the progression of feeding in the infant. In an embodiment of the present invention, the user is enabled to view the reports, as generated by the processing unit using one or more devices selected from the group comprising a smartphone, a computer, a laptop, a tablet, a personal digital assistant (PDA) and a mobile phone.

In an embodiment of the invention, the simulating breast-feeding system 100 is configured to receive an input parameter from an infant/user, a network interface, a processor, an analyzing module, a non-transitory storage element coupled to the processor with encoded instructions stored in the non-transitory storage element, wherein the encoded instructions when implemented by the processor configure the simulating breast-feeding system 100 to receive an input parameter from an infant/user, determine a physical, physiological or emotional state of the infant/user by mapping the received input parameter with a pre-stored set of parameters via the analyzing module and dynamically interacting with the infant/user based on a determined output. The pre-stored of parameters may be a plurality of infant behaviors as outlined in American academy of Pediatrics, World health organization, National Institute of child health and human development, Food and Drug administration, American academy of family physicians. Further yet, in another embodiment of the invention, the physical input parameter may be at least one of, but not limited to, motion, sleep, gestural, visual, audio or environmental factors/conditions. Moreover, the sleep related characteristics of the infant may be indicative of at least one of, duration of sleep time, number of times awake, sound sleep, light sleep and awake time. Additionally, the physiological input parameters may be at least one of, but not limited to, age, gender, race, medical history, heart rate, medication history, blood pressure, sweat, duration of feeding, number of feedings and food intake of user/infant.

Additionally, environmental conditions may affect infant activity. The environmental conditions can be at least one of, but not limited to, wind velocity, temperature, humidity, aridness, light, darkness, noise pollution, exposure to UV, airborne pollution and radioactivity. Further yet, data generated from a set of parameters corresponding to at least one of, but not limited to, user/infant reported symptoms and side effects, periodic surveys may be used to generate a personal profile of the infant/user. The data generated may in any one of, but not limited to, audio, video or an image input and further, implemented on at least one of, but not limited to a mobile communication device, body worn device, wearable device, tablet and or IoT.

Further yet, in an embodiment of the invention, a deviation from the personal profile may be alerted to the user by at least one of, a visual or color appearance, audio or sound, buzzer, vibration, fine motor skills, memory-based tasks, repeating actions, sounds or movements. Moreover, the simulating breast-feeding system 100 may comprise detection a deviation from the personal profile of the user/infant using machine learning algorithm.

Further yet, a machine learning algorithm may be employed to inform upstream processes. Additionally, in simulating breast-feeding system 100, the aggregation of the set of parameters occurs from at least one of, a mobile communication device, wearable device, smartphone, tablet, personal digital assistant (PDA) and Internet of Things device.

Further yet, in another embodiment, the simulating breast-feeding system 100 may further comprise integration with any one of a third-party application via an Application Program Interface (API) 207. This allows for 3rd party database integration, such as Electronic Medical Records (EMR), health monitoring, proxy health provisioning, remote server and, or a cloud-based server for other 207 downstream analytics and provisioning. Additionally, the completed automated responses may be saved onto a remote cloud-based server for easy access for data acquisition and archival analytics for future use.

In another embodiment of the invention, simulating breast-feeding system 100 may allow for easy saving, searching, printing, and sharing of completed automated response information with authorized participants. Additionally, simulating breast-feeding system 100 may allow for non-API applications, for example, building reports and updates, create dashboard alerts as well as sign in/verifications 207. Alternatively, sharing may be possible with less discrimination based on select privacy filters.

Figure 2:
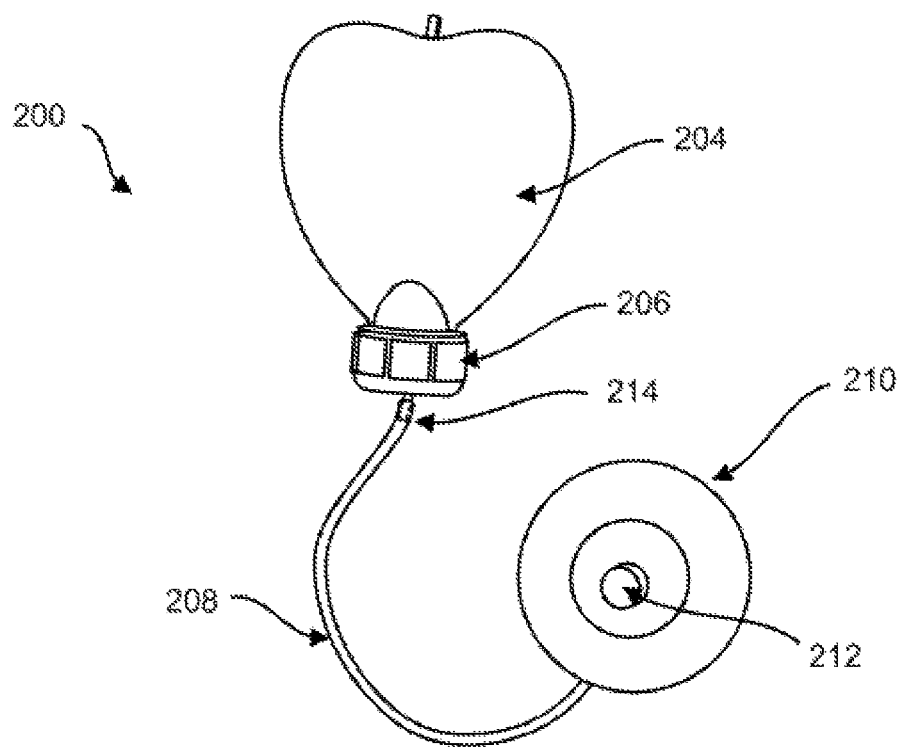
FIG. 2 illustrates an exemplary illustration with various embodiments of the disclosure that can be practiced.

FIG. 2 illustrates a simulating breast-feeding apparatus. As shown in FIG. 2, a simulating breast-feeding apparatus 200 comprises of a neck strap (not shown), an attachable refillable housing chamber 204 with sealing contraption 206 at the one end and a tube 206 linking the refillable housing chamber 204 to a prosthetic nipple 210 wherein, the prosthetic nipple 210 comprises of an opening 212 to deliver the fluid from the refillable housing chamber 204 to an infant to promote a non-latching simulating breastfeeding experience to prevent bruised, sore nipples or engorged breasts.

In an embodiment of the invention, the housing chamber 204, prosthetic nipple 210 or the tubing 208 is at least one of, a plurality of shapes, sizes, colors or opaqueness. Further yet, the refillable housing chamber 204 may be insulated to maintain at least one of, hot, cold or room temperature for the fluid. Further yet, in an embodiment of the invention, the size of the prosthetic nipple 210 may be of varying sizes depending on at least one of, but not limited to, age, weight, gender, amount of food intake of the infant.

Figure 3:
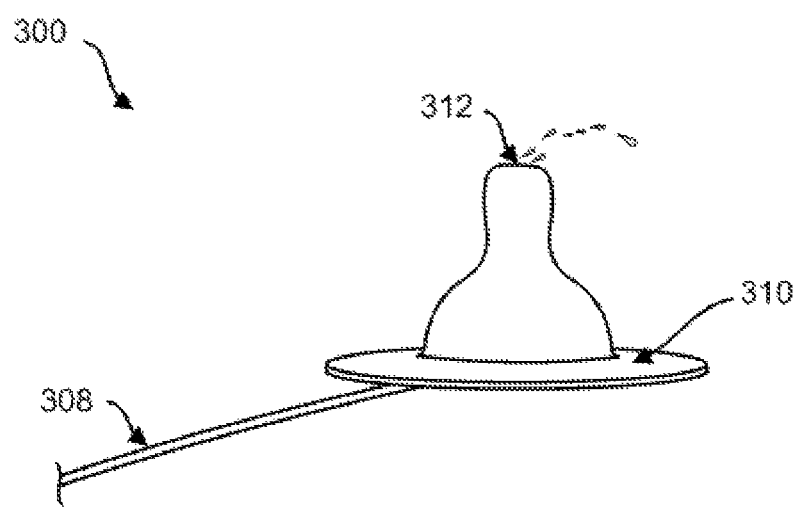
FIG. 3 illustrates an exemplary illustration of one of the embodiments invention.

FIG. 3. illustrates a side angle view of the prosthetic nipple 300. As shown in FIG. 3, a tube 308 linking the refillable housing chamber (not shown) to a prosthetic nipple 310 wherein, the prosthetic nipple 310 comprises of an opening 312 to deliver the fluid from the refillable housing chamber (not shown) to an infant to promote a non-latching simulating breastfeeding experience to prevent bruised, sore nipples or engorged breasts.

Additionally, in an embodiment of the present invention, the prosthetic nipple 310 or tubing 308 comprises of, at least one of, naturally or man-made rubber, synthetic rubber, silicone or any plastic or synthetic polymer. Further yet, in an embodiment of the invention, the back end of the prosthetic nipple 310 maybe attachable to the skin via a self-adhering glue to establish a tight seal to prevent any leakage.

Figure 4:
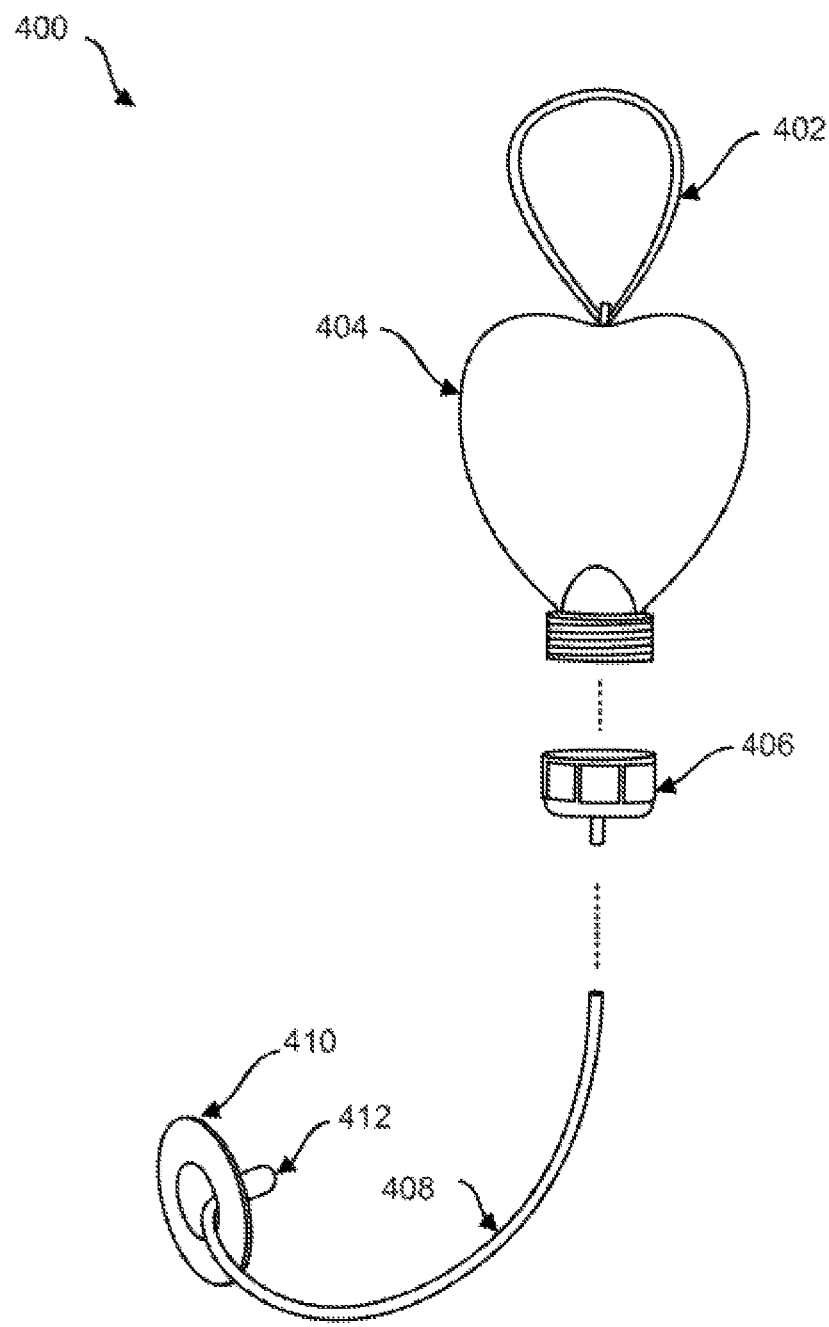
FIG. 4 illustrates an exemplary embodiment of the invention.

FIG. 4. shows an exemplary embodiment of the invention. As shown in FIG. 4, simulating breast-feeding apparatus 400 comprises of a neck strap 402, an attachable refillable housing chamber 404 with sealing contraption 406 at the one end and a tube 408 linking the refillable housing chamber 404 to a prosthetic nipple 410 wherein, the prosthetic nipple 410 comprises of an opening 412 to deliver the fluid from the refillable housing chamber 404 to an infant to promote a non-latching simulating breastfeeding experience to prevent bruised, sore nipples or engorged breasts.

In an embodiment of the invention, at least one of, neck strap, refillable housing chamber, sealing contraption, tubing or prosthetic nipple be modular. Further yet, the modular parts may be made of at least one of, non-GMO, non-toxic, organic-grade glue, BPA free or hypoallergic material. Additionally, the modular strap 402 comprises at least one of, nylon, polyester, silk, cotton, yarn, wool or fabric with a breakaway safety feature to prevent pulling or choking with or without a breakaway safety feature to prevent pulling or choking.

Further, in an alternative embodiment, the modular strap 402 may be worn as a waist belt or a shoulder strap that could be attached to a baby carrier or as an infant sling. Additionally, in an alternative embodiment of the invention, a clamp may be placed on the tubing 408 which may control fluid flow into the prosthetic nipple. Alternatively, a sensor may allow the user to stop the flow of fluid into the prosthetic nipple 410 by tapping on at least one of the modular parts. In yet another embodiment of the invention, the simulating breast-feeding apparatus may be held in any body worn garment or may be attached to a plurality of devices, for example, but not limited to, car seat, stroller, backpack or sling.

In an alternative embodiment of the invention, the strap 402 may have a built-in chamber to hold the fluid connected to the prosthetic nipple 410. The tube 408 may be embedded into the strap. Additionally, the strap 402 may be a part of a back pack, a body worn garment such as, but not limited to, sports bra, vest, t-shirt, nursing bra, arm band, chest band, top etc.

Figure 5:
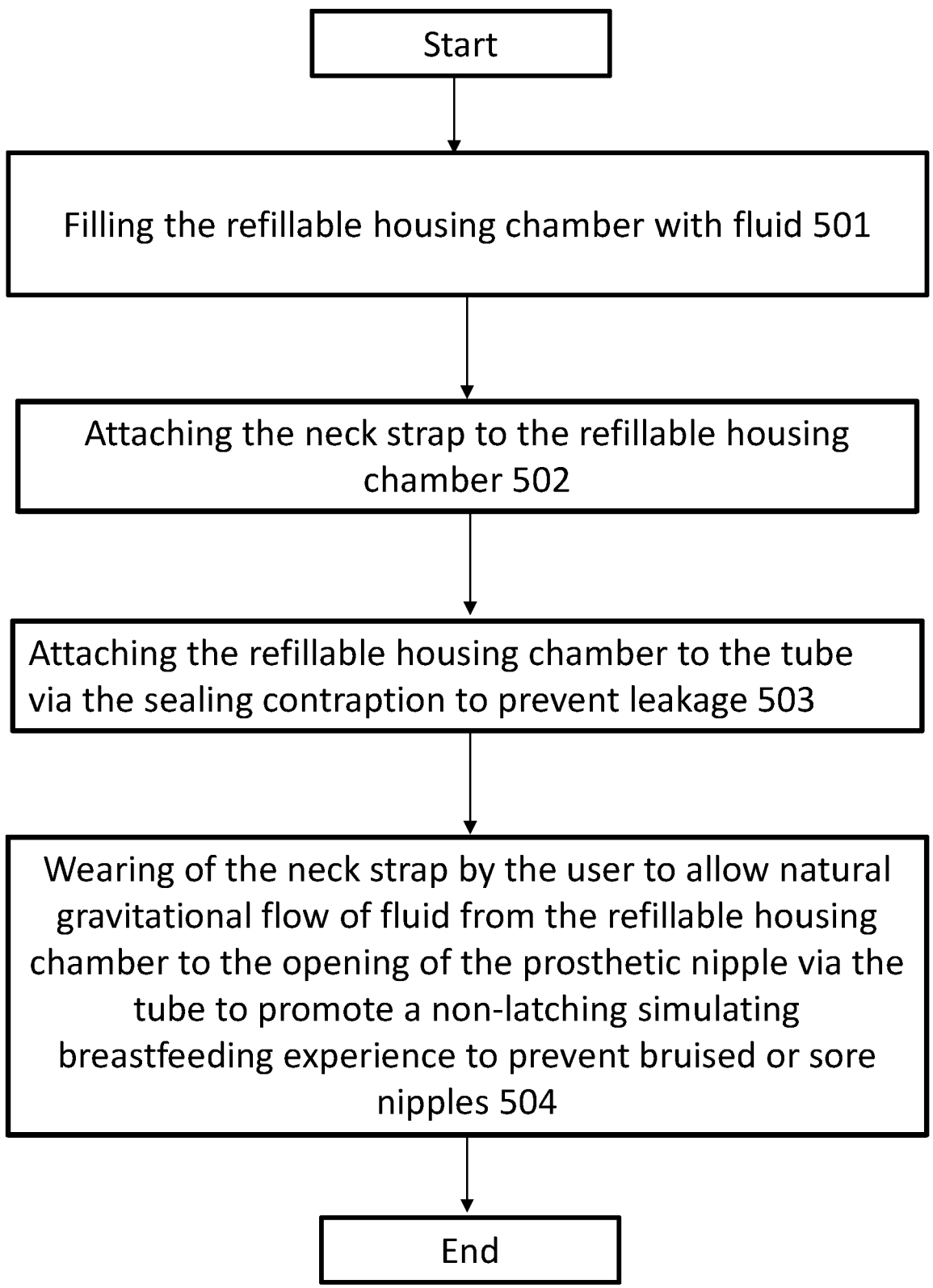
FIG. 5 illustrates a method flow of the invention.

FIG. 5 shows a method for simulated breast-feeding system. The method comprises the steps of: (1) filling the refillable housing chamber with fluid 501, (2) attaching the neck strap to the refillable housing chamber 502, (3) attaching the refillable housing chamber to the tube via the sealing contraption to prevent leakage 503 and (4) wearing of the neck strap by the user to allow natural gravitational flow of fluid from the refillable housing chamber to the opening of the prosthetic nipple via the tube to promote a non-latching simulating breastfeeding experience to prevent bruised or sore nipples 504.

Embodiments are described at least in part herein with reference to flowchart illustrations and/or block diagrams of methods, systems, and computer program products and data structures according to embodiments of the disclosure. It will be understood that each block of the illustrations, and combinations of blocks, can be implemented by computer program instructions. These computer program instructions may be provided to a processor of a general-purpose computer, special purpose computer, or other programmable data processing apparatus to produce a machine such that the instructions, which execute via the processor of the computer or other programmable data processing apparatus, create means for implementing the functions/acts specified in the block or blocks.

These computer program instructions may also be stored in a computer-readable memory that can direct a computer or other programmable data processing apparatus to function in a particular manner such that the instructions stored in the computer-readable memory produce an article of manufacture including instruction means which implement the function/act specified in the block or blocks.

The computer program instructions may also be loaded onto a computer or other programmable data processing apparatus to cause a series of operational steps to be performed on the computer or other programmable apparatus, to produce a computer implemented process such that, the instructions which execute on the computer or other programmable apparatus provide steps for implementing the functions/acts specified in the block or blocks.

In general, the word "module" as used herein, refers to logic embodied in hardware or firmware, or to a collection of software instructions, written in a programming language, such as, Java, C, etc. One or more software instructions in the unit may be embedded in firmware. The modules described herein may be implemented as either software and/or hardware modules and may be stored in any type of non-transitory computer-readable medium or other non-transitory storage elements. Some non-limiting examples of non-transitory computer-readable media include CDs, DVDs, BLU-RAY, flash memory, and hard disk drives.

In the drawings and specification, there have been disclosed exemplary embodiments of the disclosure. Although specific terms are employed, they are used in a generic and descriptive sense only and not for purposes of limitation, the scope of the invention being defined by the following claims. Those skilled in the art will recognize that the present invention admits of a number of modifications, within the spirit and scope of the inventive concepts, and that it may be applied in numerous applications, only some of which have been described herein. It is intended by the following claims to claim all such modifications and variations which fall within the true scope of the invention.

I claim:

1. A simulating flow control breast-feeding system comprising:
   a neck strap;
   an attachable refillable housing chamber with a sealing contraption at one end;
   a clamp attached to a tube to control flow of fluid, said tube linking the refillable housing chamber to a prosthetic nipple wherein;
     the prosthetic nipple comprises of an opening to deliver the fluid from the refillable housing chamber to an infant to promote a non-latching simulating breastfeeding experience to prevent bruised, sore nipples or engorged breasts;
   a sensor;
   a network interface;
   a processor;
   an analyzing module;
   a non-transitory storage element coupled to the processor and;
   encoded instructions stored in the non-transitory storage element, wherein the encoded instructions when implemented by the processor, configure the system to:
     receive an input parameter from an infant/user;

determine a physical, physiological or emotional state of the infant/user by mapping the received input parameter with a pre-stored set of parameters via the analyzing module; and dynamically interact with the infant/user based on a determined output.

2. The system of claim 1, further comprising of a sensor attached to at least one of, sealing contraption, neck strap, prosthetic nipple, tubing or the refillable housing.

3. The system of claim 1, wherein at least one of the sealing contraption, neck strap, prosthetic nipple, tubing or the refillable housing may be modular.

4. The system of claim 2, wherein the sensors is at least one of, a motion sensor, an accelerometer, a temperature, a 3D accelerometer, a gyroscope, a global positioning system sensor (GPS), a magnetometer, an inclinometer and an impact sensor.

5. The system in claim 2, further comprising of, the sensor to monitor fluid consumption to gauge if the infant is feeding for comfort or hunger.

6. The system in claim 2, further comprising of, a sensor to detect at least one of, infant temperature, heart rate, pulse rate, respiratory patterns or rhythms or accuracy of latching.

7. The system of claim 1, wherein the input parameter may be at least one of, a motion, sleep, gestural, visual, audio or environmental condition.

8. The system of claim 1, further comprising establishing a personal profile of the infant/user based on at least one set of parameters.

9. The system of claim 1, wherein deviation from the personal profile may be alerted to the user by, at least one of, a visual or color appearance, audio or sound, buzzer, vibration, fine motor skills, memory-based tasks, repeating actions, sounds or movements.

10. The system of claim 1, further comprising detecting a deviation from the personal profile of the infant/user using machine learning algorithm.

11. A simulating flow control breast-feeding apparatus comprising:

a neck strap;

an attachable refillable housing chamber with sealing contraption at an one end; and a clamp attached to a tube to control flow of fluid, said tube linking the refillable housing chamber to a prosthetic nipple wherein;

the prosthetic nipple comprises of an opening to deliver the fluid from the refillable housing chamber to an infant to promote a non-latching simulating breast-feeding experience to prevent bruised, sore nipples or engorged breasts.

12. The apparatus of claim 11, wherein the housing chamber, prosthetic nipple or the tubing is at least one of, a plurality of shapes, sizes, colors or opaqueness.

13. The apparatus of claim 11, further comprising at least one of, neck strap, refillable housing chamber, sealing contraption, tubing or prosthetic nipple be modular.

14. The apparatus of claim 11, wherein a modular parts may be made of at least one of, non-GMO, non-toxic, organic-grade glue, BPA free or hypoallergic material.

15. The apparatus of claim 11, wherein the prosthetic nipple or tubing comprises of, at least one of, naturally or man-made rubber, synthetic rubber, silicone or any plastic or synthetic polymer.

16. The apparatus of claim 11, wherein a back end of the prosthetic nipple maybe attachable to the skin via a self-adhering glue to establish a tight seal.

17. The apparatus of claim 11, wherein a size of the prosthetic nipple maybe directly proportional to any one of age, gender, weight, food intake of the infant.

18. The apparatus of claim 11, wherein the neck strap comprises at least one of, nylon, polyester, silk, cotton, yarn, wool or fabric with a breakaway safety feature to prevent pulling or choking.

19. The apparatus of claim 11, wherein the refillable housing chamber may be insulated to maintain at least one of, hot, cold or room temperature.

20. A method for simulated flow control breast-feeding system, the method comprising:

filling the refillable housing chamber with fluid;

attaching the neck strap to the refillable housing chamber;

attaching the refillable housing chamber to the tube via the sealing contraption to prevent leakage;

attaching a clamp to the tube to maintain flow control of the fluid; and wearing of the neck strap by the user to allow natural gravitational flow of fluid from the refillable housing chamber to the opening of the prosthetic nipple via the tube to promote a non-latching simulating breastfeeding experience to prevent bruised or sore nipples.

* * * * *